United States Patent [19]
Marquit

[11] Patent Number: 5,220,929
[45] Date of Patent: Jun. 22, 1993

[54] BIO-COMPATIBLE BOOT FOR IMPLANTABLE MEDICAL DEVICE

[75] Inventor: Timothy A. Marquit, San Jose, Calif.
[73] Assignee: Ventritex, Inc., Sunnyvale, Calif.
[21] Appl. No.: 770,179
[22] Filed: Oct. 2, 1991
[51] Int. Cl.⁵ .............................. A61N 1/36
[52] U.S. Cl. .................... 128/898; 128/419 P; 128/DIG. 18
[58] Field of Search .................. 623/1, 901; 128/DIG. 18, 662.06, 898, 899, 419 P; 29/447; 156/293, 85, 86; 606/42, 50, 51

[56] References Cited

U.S. PATENT DOCUMENTS

| | | | |
|---|---|---|---|
| 3,735,766 | 5/1973 | Bowers et al. | 128/419 P |
| 3,911,241 | 10/1975 | Jarrard | 606/42 |
| 3,967,995 | 7/1976 | Fabianic | 156/293 |
| 4,013,081 | 3/1977 | Kolenik | 128/419 P |
| 4,057,068 | 11/1977 | Comben | 128/419 P |
| 4,127,134 | 11/1978 | Ushakoff | 128/419 P |
| 4,911,173 | 3/1990 | Terwilliger | 128/662.06 |
| 5,000,804 | 3/1991 | Nugent | 156/86 |
| 5,061,276 | 10/1991 | Tu et al. | 623/1 |
| 5,128,146 | 7/1992 | Hirayama et al. | 623/901 |

Primary Examiner—William E. Kamm
Assistant Examiner—George Manuel
Attorney, Agent, or Firm—Steven M. Mitchell; Mark J. Meltzer

[57] ABSTRACT

A boot manufactured from a bio-compatible material is used to smooth the external shape of an implantable medical device and to seal the device against fluid intrusion.

3 Claims, 2 Drawing Sheets

BIO-COMPATIBLE BOOT FOR IMPLANTABLE MEDICAL DEVICE

BACKGROUND OF THE INVENTION

1. Field of the Invention

The present invention relates to medical devices and, in particular, to a boot made of bio-compatible material and used for smoothing the external shape of an implantable medical device.

2. Discussion of the Prior Art

In the past, implantable medical devices, have typically been housed in titanium or stainless steel containers.

The sharp corners usually incorporated into these conventional metal containers to obtain a compact design can cause patient discomfort and tissue erosion if the device interferes with the patient's bone or tissue. They are also relatively heavy.

A fabric boot/pouch has also been used over implanted pacemakers to reduce post-operative oozing and to fix the pacemaker to the tissues. See V. Parsonnet, "A Stretch Fabric Pouch for Implanted Pacemakers", Archives of Surgery, Vol. 5, No. 4, October 1972.

However the thin Dacron fabric cover provides no cushioning effect. Moreover, the fabric pouch conforms closely to the shape of the metal device container and, therefore, does not smooth the container's sharp corner radii.

SUMMARY OF THE INVENTION

The present invention provides a soft, bio-compatible boot that is used to smooth the harsh shape of implantable medical devices. The boot material is bio-compatible since it is implanted in the body with the device. The preferred material is silicone rubber which can be made by standard manufacturing processes. The use of a soft boot reduces weight and provides a soft interface with bones and tissue by reducing sharp corners with larger radii and blended, smooth surfaces.

A better understanding of the features and advantages of the present invention will be obtained by reference to the following detailed description and accompanying drawings which set forth an illustrative embodiment in which the principles of the invention are utilized.

DETAILED DESCRIPTION OF THE INVENTION

Figure 1:
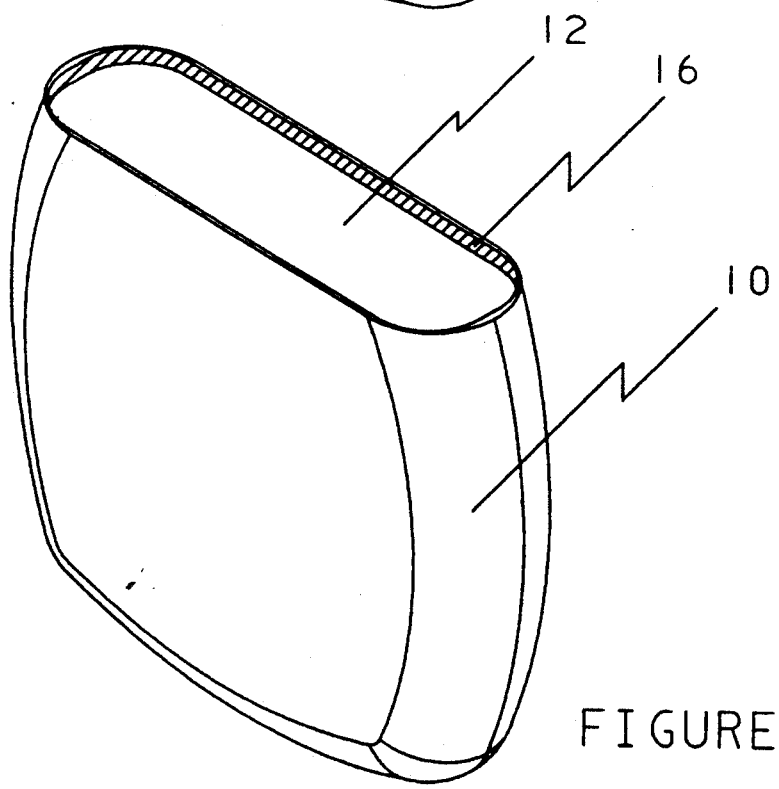
FIG. 1 is an isometric view illustrating a bio-compatible boot in accordance with the present invention and having adhesive at the edge of its opening.

FIG. 1 shows a boot 10 made of bio-compatible material. While the preferred material is silicone rubber, which can be made in accordance with standard manufacturing techniques, the boot may also be made of other bio-compatible material, such as, for example, ultra-high molecular weight polyethylene, polyurethane or expoxy. However, while these materials have the same smoothing capability as silicone rubber, they are rigid and do not provide the same cushioning effect for the implantable device as does silicone rubber.

As shown in FIG. 1, the interior of the boot 10 is hollow and provided with an opening 12 such that the boot 10 is adapted to receive an implantable medical device, such as a defibrillator, that is utilizable for delivering therapy to a patient.

Conventional implantable medical devices are designed to be as small and as light as possible. This can result in designs for these devices that have small, sharp corner radii. As further shown in FIG. 1, the boot 10 is designed with larger radii and blended, smooth surfaces to lessen the possibility of patient discomfort and tissue erosion.

Figure 2:
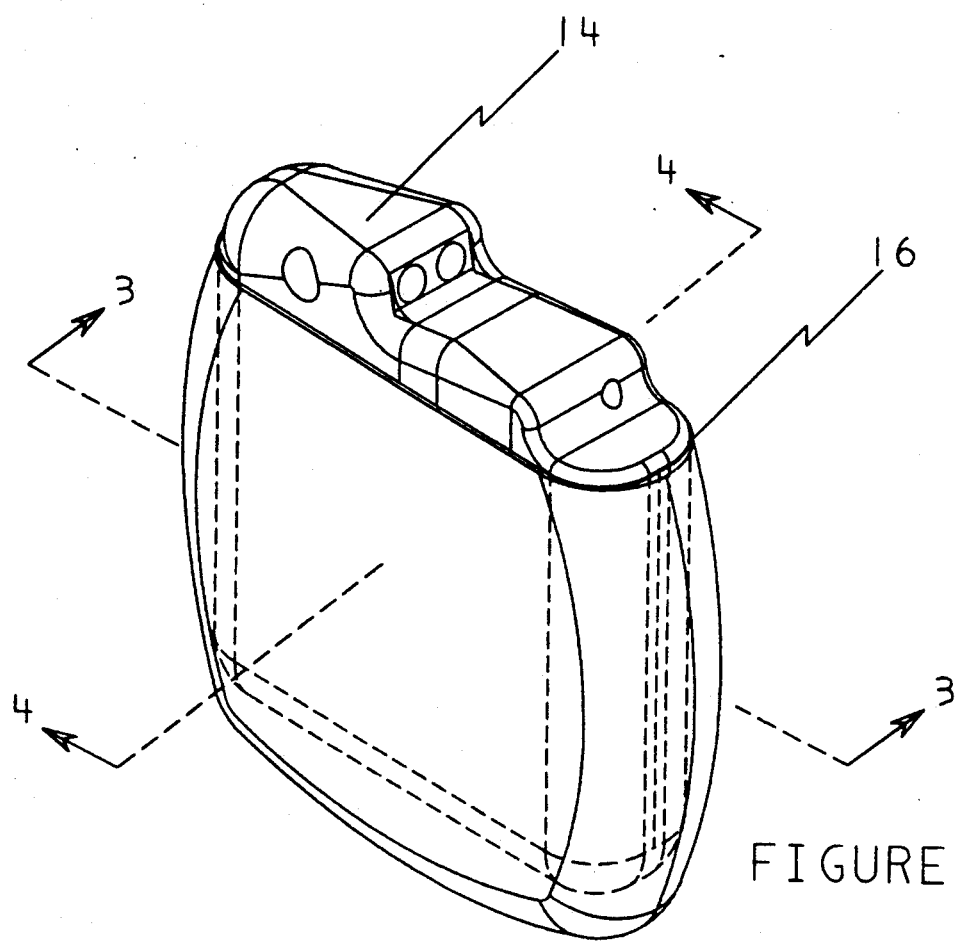
FIG. 2 is an isometric view illustrating a bio-compatible boot in accordance with the present invention mounted on an implantable medical device.

FIG. 2 shows the boot 10 mounted on an implantable medical device 14.

Figure 3:
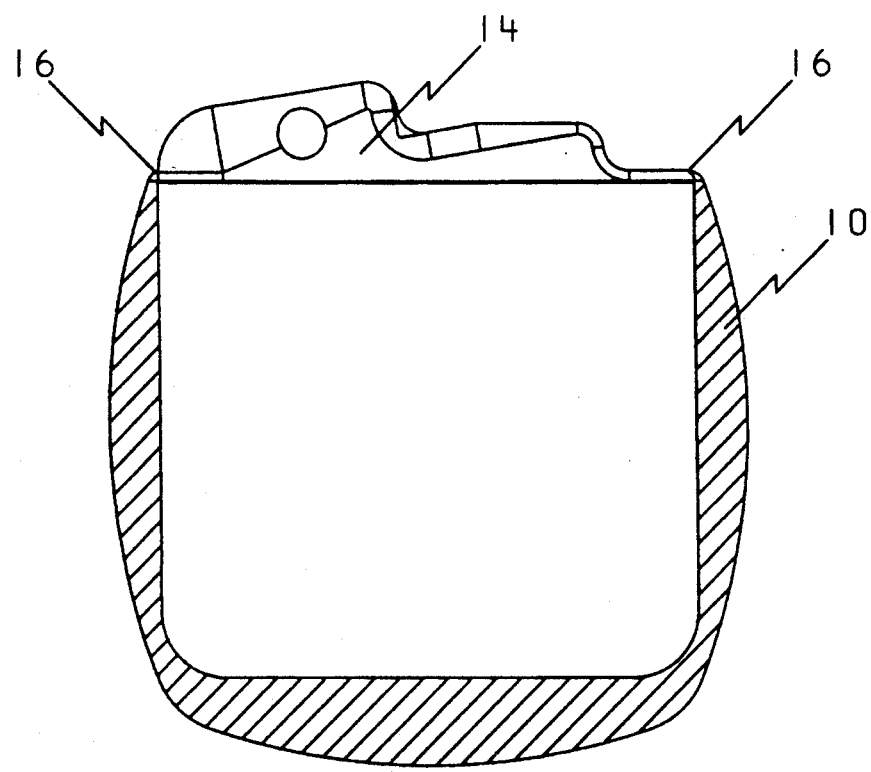
FIG. 3 is cross-sectional view taken along line 3—3 in FIG. 2 and illustrating a bio-compatible boot in accordance with the present invention mounted on an implantable medical device.
Figure 4:
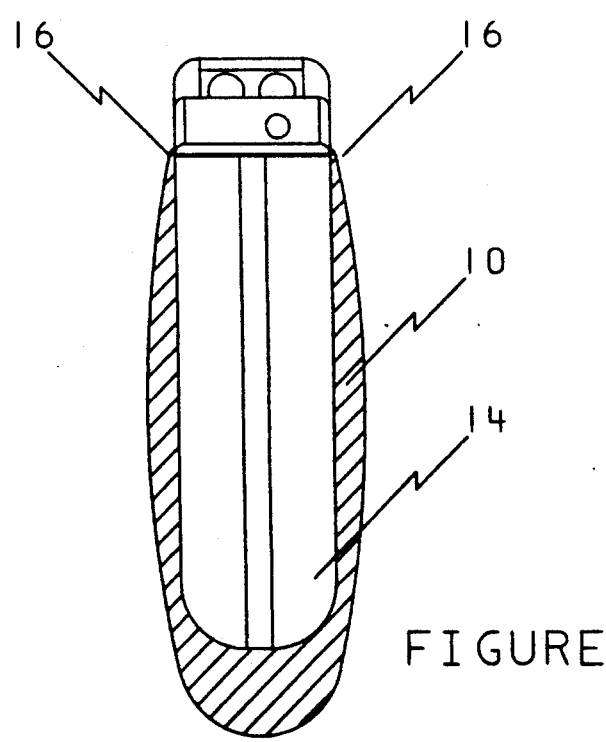
FIG. 4 is cross-sectional view taken along line 4—4 in FIG. 2 and illustrating a bio-compatible boot in accordance with the present invention mounted on an implantable medical device.

FIGS. 3 and 4 show cross-sectional views of the boot 10 mounted on device 14.

The boot 10 must be seated tightly against the medical device 14 to prevent fluid intrusion. As shown in FIGS. 1–4, this can be accomplished by applying medical adhesive 16, such as, for example, Dow Corning Silastic Medical Adhesive, Type A or equivalent, along the edge of the boot 10, sealing the boot 10 against the device 14.

In an alternate method of sealing the silicone rubber boot 10 against the device 14, the boot 10 is made to be slightly undersized relative to the medical device 14. The boot 10 is then expanded by spraying it with freon or immersing it in freon. The expanded boot 10 is then slid over the defibrillator and, as the freon dissapates, the boot 10 returns to its normal size, contracts, and becomes a press fit on the device 14, thereby preventing fluid intrusion.

Those skilled in the art will readily appreciate that the general shape of the boot 10 will depend on the shape of the device 14 that it is going to cushion.

It should be understood that various alternatives to the embodiment of the invention described herein may be employed in practicing the invention. It is intended that the following claims define the scope of the invention and that apparatus and methods within the scope of these claims and then equivalents be covered thereby.

What is claimed is:

1. A method of making an implantable medical apparatus, the method comprising:

(a) introducing a medical device for delivering therapy to a patient into a boot made of bio-compatible material and having an opening formed therein such that the boot is adapted to receive the medical device; and (b) sealing the boot to the medical device by applying adhesive at the interface between the edge of the boot opening and the medical device to prevent fluid intrusion between the boot and the medical device.

2. A method of making an implantable medical apparatus, the method comprising:

(a) expanding a boot made of bio-compatible material and having an opening formed therein, the opening being undersized in its contracted state with respect to the size of the medical device such that the opening is adapted to receive a medical device;

(b) sliding the medical device into the opening while the opening is expanded; and (c) contracting the opening such that the boot forms a press fit on the medical device, thereby preventing fluid intrusion into the interface between the boot and the medical device.

3. A method of making an implantable medical apparatus, the method comprising:

(a) applying freon to a boot made of bio-compatible material and having an opening formed therein, the opening being undersized in its contracted state with respect to the size of a medical device, such that the opening expands to be adapted to receive the medical device;

(b) sliding the medical device into the opening while the opening is expanded; and (c) contracting the opening as the freon dissapates such that the boot forms a press fit on the medical device, thereby preventing fluid intrusion between the edge of the boot opening and the medical device.

* * * * *